United States Patent
Koller et al.

[11] Patent Number: 5,886,789
[45] Date of Patent: Mar. 23, 1999

[54] OPTICAL SURFACE TESTING MEANS FOR LINEARLY MOVING, TAPE-LIKE MATERIALS

[75] Inventors: Albrecht Koller; Bernd Scholtysik, both of München, Germany

[73] Assignee: EMTEC Magnetics GmbH, Ludwigshafen, Germany

[21] Appl. No.: 802,909

[22] Filed: Feb. 20, 1997

[30] Foreign Application Priority Data

Mar. 1, 1996 [DE] Germany ................. 196 07 793.1

[51] Int. Cl.⁶ ............................................. G01N 21/84
[52] U.S. Cl. ...................... 356/430; 356/238; 356/431; 250/559.4
[58] Field of Search .................... 356/429–430, 356/238, 431; 250/559.4, 559.44, 559.45, 559.46

[56] References Cited

U.S. PATENT DOCUMENTS

| | | | |
|---|---|---|---|
| 3,584,225 | 6/1971 | Linemann | 365/238 |
| 3,972,624 | 8/1976 | Klein et al. | 356/200 |
| 4,595,840 | 6/1986 | Puumalainen | 250/572 |
| 5,047,652 | 9/1991 | Lisnyansky et al. | 356/429 |
| 5,118,195 | 6/1992 | Dobbie | 356/430 |
| 5,130,555 | 7/1992 | Suzuki et al. | 250/559 |
| 5,283,623 | 2/1994 | Muhlberg et al. | 356/238 |
| 5,357,335 | 10/1994 | Sparks et al. | 356/237 |
| 5,461,481 | 10/1995 | Bowen et al. | 356/430 |

FOREIGN PATENT DOCUMENTS

| | | |
|---|---|---|
| 306 742 | 3/1989 | European Pat. Off. . |
| 32 12 438 | 4/1982 | Germany . |
| 1103491 | 2/1968 | United Kingdom . |

*Primary Examiner*—Robert Kim
*Attorney, Agent, or Firm*—Keil & Weinkauf

[57] ABSTRACT

A surface testing device, operating by reflection, for linearly moving, tape-like materials, for example paper or polymer films, is suitable for automatic online registration of linear irregularities transverse to the direction of movement. The testing device includes a suitable test distance, at least two optical inspection units and at least one electronic circuit arrangement for detecting both the individual signals of the inspection units and the coincidence signals. In addition, a magnetic information medium wound in the form of a roll on a hub is tested by the surface testing device and carries a machine-readable and/or visually readable quality identification.

11 Claims, 2 Drawing Sheets

OPTICAL SURFACE TESTING MEANS FOR LINEARLY MOVING, TAPE-LIKE MATERIALS

BACKGROUND OF THE INVENTION

1. Field of the Invention

The present invention relates to a surface testing means, operating by reflection, for linearly moving, tape-like materials, in particular for an information-carrying tape coated with a magnetic recording layer.

2. Description of the Related Art

When tape-like materials of this type are used, they have to meet high requirements with regard to freedom from errors. In particular, linear surface irregularities transverse to the running direction of the tape are undesirable. These form in particular as a result of creasing during their production in a tape coating machine. In this procedure, a tape-like substrate is unwound from a roll, transported in its running direction through the machine by means of positively driven rollers, coated and finally wound onto a second roll under tension.

It is known that transverse creases can form in the outer wound layer, for example as a result of brief changes in the winding speed or in the tension, and are included in the roll during further winding. As a result of the action of the tension of subsequent wound layers, this leads to permanent, linear deformations of the tape surface. These may render the relevant roll useless. Since such creasing cannot be completely avoided with the conventional winding means, there is a need for suitable surface testing means for detecting the creases or the linear deformations of the tape-like material which are caused by creasing.

An appropriate optical testing means is disclosed, for example, in U.S. Pat. No. 5,130,555. According to this, a pattern of linear, parallel stripes is projected onto the surface of a continuously moving tape-like material and the line pattern reflected by the surface is electronically evaluated. A crease is detected if the reflected pattern deviates from the original with regard to linearity. The tape crease can then be eliminated by a suitable tape guide means.

This technical procedure is, however, very expensive because, for example, a complex test system comprising video camera, video processor and subsequent electronic data processing is required.

This is true particularly when a plurality of tape strips of the tape-like material are to be tested simultaneously, for example on a longitudinal slitting machine for magnetic information media. It is also possible that very fine linear irregularities will not be detected, owing to the limited optical resolution of the imaging system and the digitizing of the reflected pattern. U.S. Pat. No. 5,357,335 and DE-C 32 12 438, too, are not completely satisfactory with respect to reliable registration of fine, linear irregularities of the tape surface. These documents merely provide optical evidence of large, local layer defects on a coated tape, having, for example, a defect diameter greater than 0.5 mm.

SUMMARY OF THE INVENTION

It is an object of the present invention to provide an improved surface testing means which is simply and economically constructed, has a high probability of detecting fine linear irregularities of the tape surface and is suitable for automatic online inspection of the tape surface. The means should furthermore be just as suitable for the simultaneous testing of a plurality of tape strips as for the inspection of a single tape strip. We have found that this object is achieved by surface testing means, operated by reflection, for linearly moving, tape-like materials for automatic online registration of linear irregularities (6) transverse to the direction of movement on the tape, comprising:

a) tape guide means consisting of at least two stationary rods (1, 1') and intended for stabilizing the tape running along at least one test distance (2), the rod axes being oriented perpendicular to the direction of movement, b) at least two optical inspection units (3, 3') which scan the same surface of the tape-like material and are assigned to spatially separated test areas of the test distance and each of which contains optical transmitting means (4, 4') and receiving means (5, 5') and c) at least one electronic circuit arrangement for registering error signals, the individual analog signals $E_1$ and $E_2$ of the receiving means (5, 5') being compared with a first, settable trigger threshold $S_1$ and first error signals $F_1$ or $F_2$ being registered therefrom if $E_1$ or $E_2$ exceeds the threshold $S_1$, and pairs of individual signals $E_1$, $E_2$ being tested for coincidence in a coincidence circuit having a settable time window $\Delta t$ and, if coincidence is present, second error signals $F_{12}$ being registered if both coincident individual signals $E_1$ and $E_2$ exceed a second, settable trigger threshold $S_2$, $S_2$ being more critical than $S_1$.

Also included are further advantageous practical embodiments of the invention. A magnetic information medium which is tested by the novel testing means and carries an appropriate identification is also novel. Embodiments of the invention are contained in the description below and in the drawings.

DETAILED DESCRIPTION OF THE INVENTION

Figure 1A:
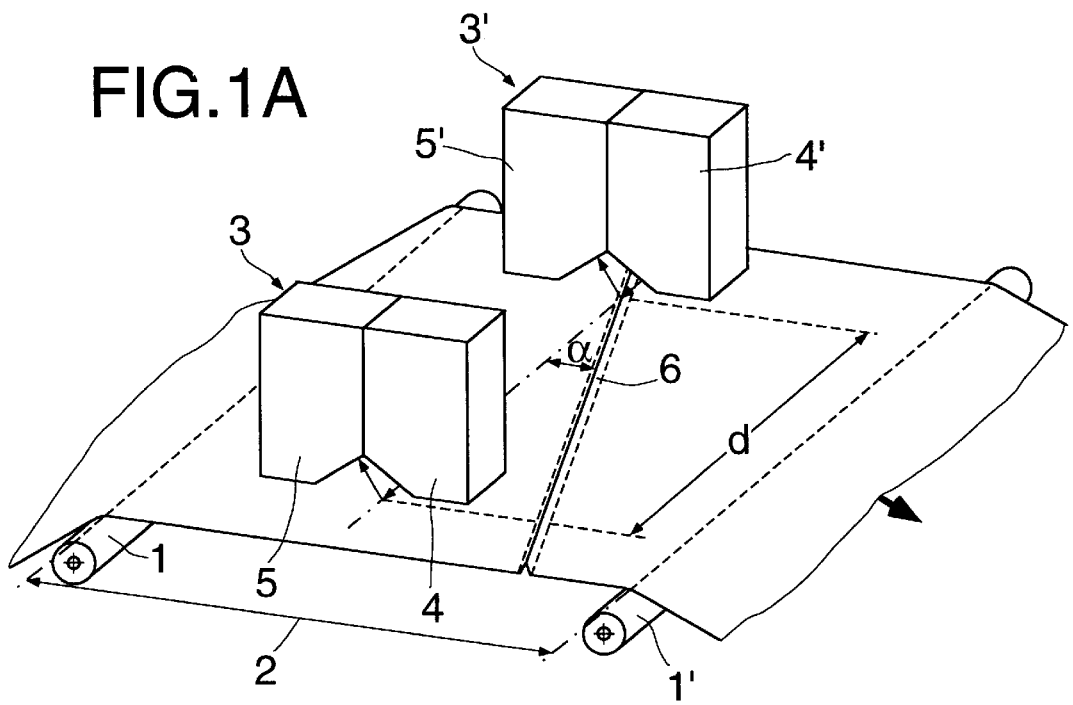
FIG. 1a shows a testing means for a single tape according to the present invention.

The invention comprises a suitable test distance (2) of the tape-like material moving continuously in the running direction, which test distance is bounded by at least two stationary tape guide rods (1, 1'), with at least two spatially fixed inspection units (3, 3') which scan the same surface of the tape-like material without contact and at least one electronic circuit arrangement for evaluating the receiver signals (5, 5'), and for doing so both as individual signals for registering local defects and in coincidence for registering linear irregularities (6) transverse to the direction of movement. All three components cooperate synergistically, resulting in a considerably increased sensitivity of detection. The use of a microcomputer which gathers the error signals and outputs test documents for each individual tested tape strip is advantageous.

Figure 1B:
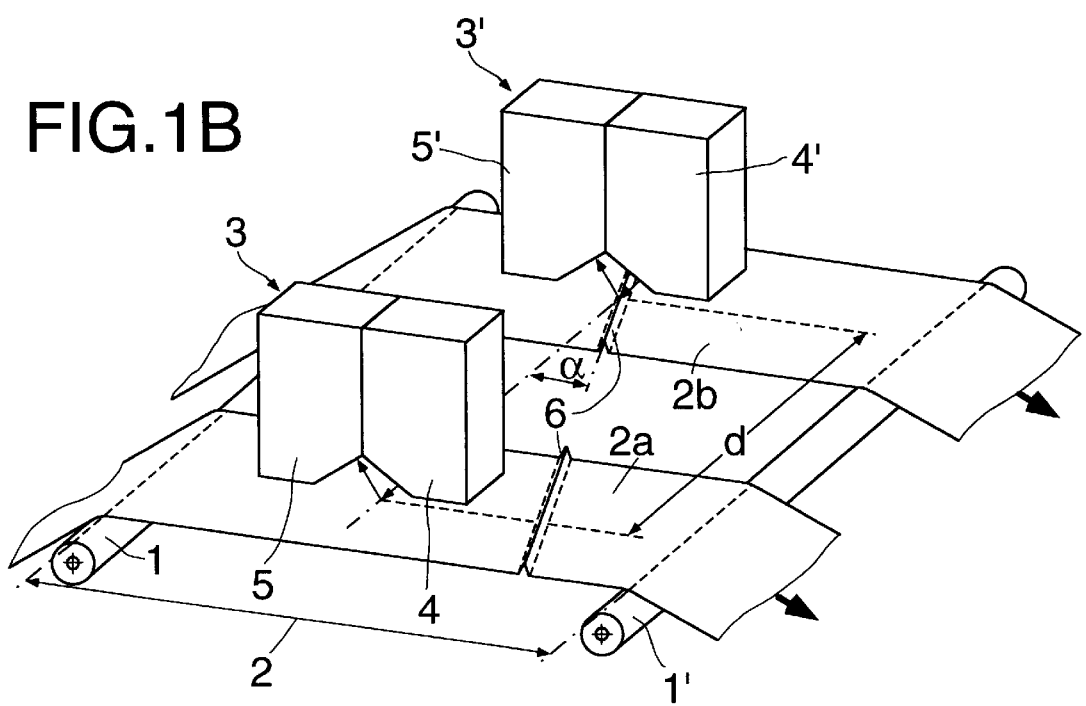
FIG. 1b shows a testing means for two spatially separated tapes (2a, 2b) according to the present invention.

For the purposes of the present invention, the test distance (2) may comprise either only a single web (FIG. 1a) or at least two separate webs (FIG. 1b). In the case of FIG. 1b, the webs (2a, 2b) originate from the same original roll and are formed therefrom by longitudinal slitting on a slitting machine known per se. The test distance (2) is bounded in the direction of movement by tape guide rods (1, 1').

The tape guide rods (1, 1') consist of cylindrical rods which have a circular cross-section and are rigidly fastened to a rigid frame arranged laterally adjacent to the tape and over whose lateral surfaces the tape-like material glides with contact. In comparative experiments, it was in fact found that this ensures very vibration-stable tape running along the test distance (2). Alternative embodiments of the tape guidance, for example by rotating rollers or air bearing rods which have a lateral surface permeable to compressed air and form an air cushion on which the tape-like material glides without contact, can on the other hand cause vibrations of the tape strip along the test distance (2) perpendicular to the tape surface. The longitudinal axes of the rods are parallel with one another and oriented perpendicular to the direction of movement of the test material.

The exact dimensions of the tape guide rods (1, 1') and the design of the frame and the exact fastening of the rods on the frame are not important. The rod length is chosen so that it is greater than the width of the inspected tape strip so that the rod ends project on both sides of the tape strip (FIGS. 1a, 1b). The distance between the tape guide rods should be as small as possible so that external influences, for example air currents, do not cause any additional vibrations of the tape along the test distance (2) and perpendicular to the surface.

In an advantageous embodiment of the invention, tape guide rods (1, 1') consist of electrically conductive, earthed material, for example of a metallic alloy, so that the lateral surface of the rods and the tape surface gliding thereon cannot become electrically charged. It is known that an electrical surface charge and tape-like materials leads, inter alia, to increased dust deposition and hence to undesirable point-like surface indentations in the wound material roll.

In a further advantageous embodiment, the lateral surface of the rods (1, 1') consists of hardened steel having a polished surface in order to avoid damage to the tape surface gliding thereon.

In a further advantageous embodiment, the numerical value of the average peak-to-valley height $R_z$ of the lateral surface of the rods (1, 1') should be less than 0.2 $\mu$m at every point of the contact surface in order to avoid damage to the tape surface.

Furthermore, it is advantageous, with respect to the present invention and for avoiding damage to the tape surface, if the surface of the tape-like material is coated with a friction-reducing coat on the side gliding over the rods, which coat consists, for example, of a polymeric coating film which contains finely divided inorganic pigments. This is the case in particular with tape-like magnetic information media which are coated with a recording layer which contains magnetic pigments. Such tape-like material whose structure and production are known per se and do not form part of the invention is advantageously guided with the appropriate layer surface, which is also very smooth and usually has an average peak-to-valley height $R_z$ of less than 0.2 $\mu$m, over the stationary tape guide rods (1, 1') and in contact with said rods. With an appropriate spatial arrangement of the testing means, it is possible to test that surface of the tape-like material which is opposite to the coating as well as the coating surface.

It is also advantageous if the tape guidance in contact with the tape guide rods (1, 1') is such that the tape strips at least partly wrap around the lateral surfaces of the rods (1, 1'). This serves for stabilization of the tape running along the test distance (2), in particular for avoiding tape vibrations perpendicular to the tape surface. The respective angle of wrap should preferably be greater than 10$, particularly preferably from 20° to 80°.

The inspection units (3, 3') comprise optical transmitting means (4, 4') and receiving means (5, 5') which are mounted on one side of the tape-like material and inspect the same tape surface in reflection. Transmitting means (4, 4') and receiving means (5, 5') may either consist of spatially separated units or each be present in a closed housing. In the specific embodiment of the invention, the latter arrangement was advantageously chosen because the compact design also permits the use of a plurality of identical inspection units, for example on a winding means of a longitudinal slitting machine for magnetic tapes.

According to the invention, transmitting and receiving means of the inspection units (3, 3') act on spatially separated surface regions which are not both in the direction of movement of the tape-like material. In the case of FIG. 1a, it is advantageous if the connecting line between the mid-points of the areas covered by the units (3, 3') on the tape surface is perpendicular to the direction of movement. In the case of FIG. 1b with two separate tape strips (2a, 2b), this applies appropriately for the original tape-like material not yet separated. Thus, the linear irregularities (6) of the tape surface which were described at the outset and are transverse to the direction of movement can be detected in coincidence by both inspection units (3, 3').

The transmitting means (4, 4') can in principle consist of any suitable light source. In the specific case, they consisted of infrared light emitting diodes which emit light having a maximum intensity at 875 nm. The receiving means (5, 5') are appropriately selected light detectors, for example phototransistors. A suitable front lens can improve the focusing of the rays of emitted light onto the tape surface.

The fastening of the inspection units should be chosen so that mechanical vibrations of the arrangement are avoided.

In an advantageous embodiment, the inspection units (3, 3') are arranged spatially in such a way that the optical axes of the transmitting (4, 4') and receiving means (5, 5') are each in the plane of reflection of the light and that the point of intersection of the axes lies on the surface to be tested. It is also advantageous if the angle between the optical axis of each receiving means (5, 5') and the surface normals is equal to the angle of reflection of the light emitted by the transmitting means (4, 4'). It is known that this results in a high sensitivity of detection of surface irregularities of the tape-like material.

Depending on the spatial intensity distribution of the light scattered back from the surface, ie. the back-scattering characteristic, it may however also be advantageous to turn the inspection units so that the optical axis of the receiving means (5, 5') is not arranged in the direction of the reflected light. The optimum arrangement of the inspection units (3, 3') is determined in relation to the tape surface to be tested, in suitable preliminary experiments in the novel surface testing arrangement.

Figure 2:
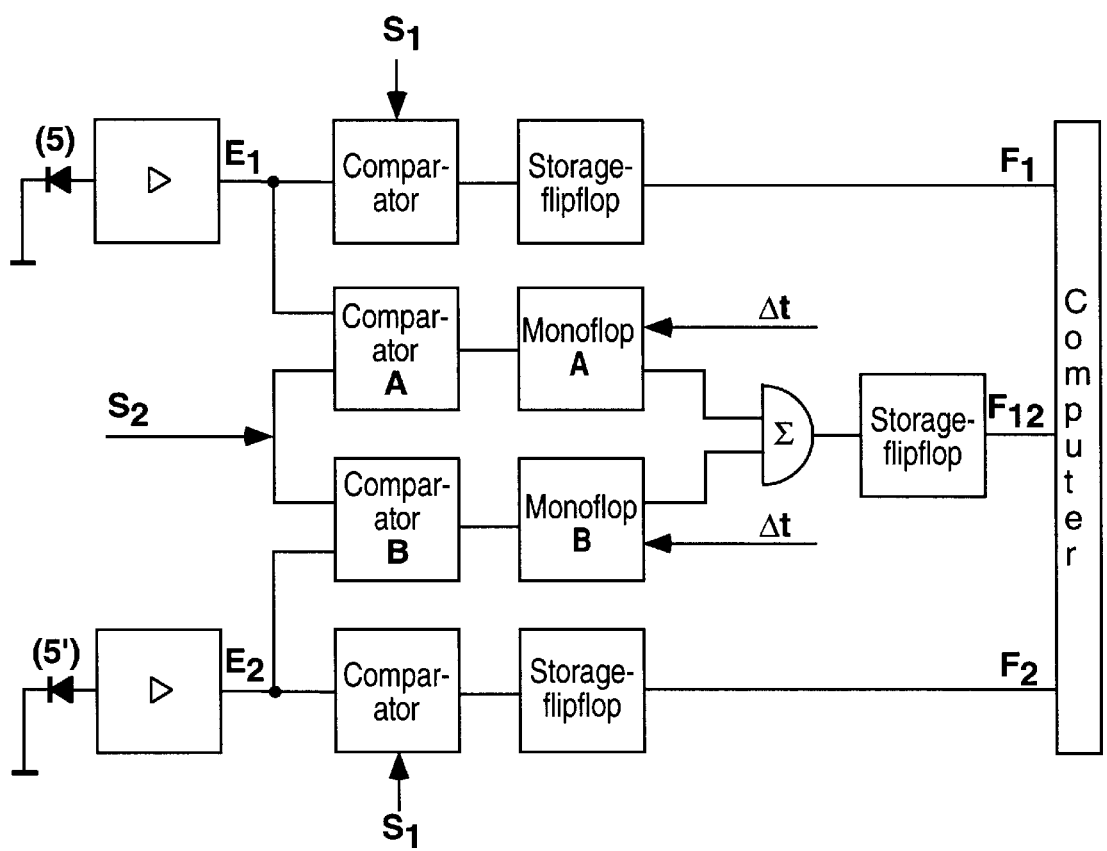
FIG. 2 shows the electronic circuit arrangement belonging to two inspection units (3, 3') according to the present invention.

The electronic circuit arrangement for processing the signals of the receiving means (5, 5') consists, in FIG. 2, of two linear signal paths and a common coincidence path with discrete or integrated amplifiers, comparators and flip-flop elements, which are known per se as components (FIG. 2). In the specific case, the comparator thresholds ($S_1$, $S_2$) can be preselected manually or set by a microcomputer. The fact that the threshold $S_2$ of the coincidence circuit can be chosen to be substantially lower than the threshold $S_1$ of the linear signal paths is a particular advantage because noncoincident individual signals ($E_1$, $E_2$) are not registered in the coincidence circuit and the noise level of the coincidence is lower than the noise level of the individual signals. In the specific case, $S_1$ was about 3 V and $S_2$ about 1.5 V.

The pulse length $\Delta t$ of the digital signals of the monoflop modules determines the coincidence resolution time and is likewise selected manually or by the computer. In suitable preliminary experiments, using suitable tape samples which have linear irregularities (6) transverse to the direction of movement of the tape, the value of $\Delta t$ can be determined as the minimum value which is required for a coincidence event. However, in the case of FIG. 1a and in the specific embodiment, it is also possible to calculate $\Delta t$ from the formula $$\Delta t = \frac{d}{v} \cdot \tan\alpha \qquad (I)$$

In the formula, v is the tape speed, d is the distance between the test areas of the inspection units, perpendicular to the direction of movement, and $\alpha$ is the azimuthal angle between the direction of the linear irregularity and the normal to the direction of movement in the test plane. In the specific case according to FIG. 1a, the tape speed was 8 m/s, the distance d was about 13 mm and the angle $\alpha$ was 80$, resulting in $\Delta t$=9.2 ms. This formula can in principle also be used in the case of FIG. 1b, but it may then be necessary also to take into account the difference between the running lengths of the test strips (2a, 2b) up to the test areas of the inspection units (3, 3'). In the specific case, linear irregularities were detectable in the azimuthal angle range of from 0° to about 80°.

The mode of action of the circuit arrangement according to FIG.2 is known to a person skilled in the art. In connection with the present invention, only the generation of the coincidence error signal $F_{12}$ is to be described below:

If, for example, a crease (6) moves at an azimuthal angle $\alpha$ through the test distance (2) and reaches the inspection unit (3) first and the inspection unit (3') after a time $\Delta t$, a first, individual analog signal $E_1$ appears at an input of comparator A and a second, delayed signal $E_2$ at an input of comparator B. If the individual signals ($E_1$, $E_2$) exceed the chosen coincidence threshold $S_2$, the comparators trigger the monoflop stages monoflop A and monoflop B. Square signals having a preselected pulse duration which is at least as large as $\Delta t$ appear at the output of monoflops A and B. If the time between the monoflop pulses, which corresponds to the delay of the individual analog signals ($E_1$, $E_2$), is smaller than their pulse duration, both inputs of the AND gate are simultaneously set and the storage flip-flop counts a coincidence error event $F_{12}$.

For automatic registration of defects in linearly moving, tape-like materials, it is advantageous to monitor the contents of the storage flip-flops with the aid of a microcomputer. This gathers the linear or coincident error signals which have occurred for each individual tape strip and, after a preselectable running length, transmits the cumulative numbers of defects for each tape strip to a suitable output unit, for example a printer, bar code printer and/or magnetic stripe recorder. The flip flops are then reset to zero and are ready for the next defect-counting run.

The novel circuit arrangement is not limited only to the embodiment shown in FIG. 2. The circuit is also intended to include alternative implementations provided that separate linear signal paths and a common coincidence circuit for the detection of the error signals ($F_1$, $F_2$, $F_{12}$) from pairs of inspection units (3, 3') are provided. For example, individual components shown in FIG. 2 can be integrated on a semiconductor module or wholly or partly simulated as a numerical program in the computer.

If more than two inspection units are used simultaneously, a correspondingly larger number of identically designed circuit arrangements for error signal determination with corresponding coincidence paths may be used.

A surface testing means, operating by reflection, for linearly moving, tape-like materials, for example paper or polymer films, is suitable for automatic online registration of linear irregularities transverse to the direction of movement. The testing means comprises a suitable test distance, at least two optical inspection units and at least one electronic circuit arrangement for detecting both the individual signals of the inspection units and the coincidence signals. The present invention also relates to a magnetic information medium which is wound in the form of a roll on a hub and is tested by the surface testing means and carries a machine-readable and/or visually readable quality identification.

We claim:

1. A surface testing means, operated by reflection, for linearly moving, tape-like materials for automatic online registration of linear irregularities (6) transverse to the direction of movement on the tape, comprising:
    a) tape guide means consisting of at least two stationary rods (1, 1') for stabilizing the tape running along at least one test distance (2), the rod axes being oriented perpendicular to the direction of movement, each of the rods (1, 1') being cylindrical and having a lateral surface which has an average peak-to-valley height $R_z$ of less than 0.2 $\mu$m, and which is in contact with the same surface of the tape-like material;
    b) at least two optical inspection units (3,3') which scan the same surface of the tape-like material and are assigned to spatially separated test areas of the test distance and each of which contains optical transmitting means (4, 4') and receiving means (5, 5'); and
    c) at least one electronic circuit arrangement for registering error signals, individual analog signals $E_1$ and $E_2$ of the receiving means (5, 5') being compared with a first, settable trigger threshold $S_1$ and first error signals $F_1$ or $F_2$ being registered therefrom if $E_1$ ir $E_2$ exceeds the threshold $S_1$, and pairs of individual signals $E_1$, $E_2$ being tested for coincidence in a coincidence circuit having a settable time window $\Delta t$ and, if coincidence is present, second error signals $F_{12}$ being registered if both coincident individual signals $E_1$ and $E_2$ exceed a second, settable trigger threshold $S_2$, $S_2$ being more critical than $S_1$.

2. A surface testing means as claimed in claim 1, wherein each inspection unit (3, 3') is arranged spatially in such a way that the optical axis of each receiving means (5, 5') is in the plane of reflection of the light, which plane contains the optical axis of the transmitting means (4, 4') and is perpendicular to the tested tape surface.

3. A surface testing means as claimed in claim 2, wherein the angle between the optical axis of each receiving means (5, 5') and the direction of the surface normals of the test distance (2) is equal to the corresponding angle of incidence between the direction of surface normals and the optical axis of each transmitting means (4, 4').

4. A surface testing means as claimed in claim 1, wherein infrared light having a wavelength greater than or equal to 700 nm is used for testing.

5. A surface testing means as claimed in claim 4, wherein the optical transmitting means (4, 4') consist of infrared diodes which emit infrared light having a wavelength of about 875 nm, the optical receiving means (5, 5') consisting of phototransistors.

6. A surface testing means as claimed in claim 1, wherein the cylindrical rods consist of electrically conductive material and are grounded.

7. A surface testing means as claimed in claim 1, wherein the cylindrical rods (1, 1') consist of a hardened metallic alloy.

8. A surface testing means as claimed in claim 1, wherein that surface of the tape-like material which is in contact with each cylindrical rod is formed by an abrasion-resistant coat of a tape-like substrate, and the coat consists of a polymeric coating film which contains finely divided inorganic pigments.

9. A surface testing means, operating by reflection, on a slitting machine for magnetic information media as claimed in one or more of claims 1–5, 6, and 7–8, wherein the tape-like material along the test distance (2) consists of at least two tape strips (2a, 2b), each of which is scanned by one of the two optical inspection units (3, 3'), the error signals ($F_1$, $F_{12}$) of the first tape strip (2a) and the error signals ($F_2$, $F_{12}$) of the second tape strip (2b) and the running length of the tape strips (2a, 2b) being automatically registered.

10. A magnetic information medium which is wound in the form of a roll on a hub and carries, on its outer roll surface, a machine-readable or visually readable quality identification which is derived from the automatically registered error signals as claimed in claim 9.

11. A surface testing means according to claim 7, wherein the cylindrical rods (1, 1') consist of hardened steel.

* * * * *